United States Patent
Achter et al.

[11] Patent Number: 5,939,619
[45] Date of Patent: Aug. 17, 1999

[54] METHOD AND APPARATUS FOR DETECTING LEAKS IN PACKAGING

[75] Inventors: Eugene K. Achter, Lexington; Jonathan E. Bosworth; Helmut Klotzsch, both of Acton, all of Mass.

[73] Assignee: True Technology, Inc., Newton, Mass.

[21] Appl. No.: 08/982,728

[22] Filed: Dec. 2, 1997

Related U.S. Application Data

[60] Provisional application No. 60/032,229, Dec. 2, 1996, provisional application No. 60/032,962, Dec. 13, 1996, provisional application No. 60/048,129, May 30, 1997, and provisional application No. 60/062,350, Oct. 15, 1997.

[51] Int. Cl.⁶ ........................................... G01M 3/04
[52] U.S. Cl. ........................................ 73/40.7; 73/49.3
[58] Field of Search .................. 73/40.7, 49.3, 73/52

[56] References Cited

U.S. PATENT DOCUMENTS

| | | | |
|---|---|---|---|
| 3,555,884 | 1/1971 | Yamamoto et al. | 73/49.3 |
| 3,762,212 | 10/1973 | Morley et al. | 73/40.7 |
| 5,163,315 | 11/1992 | Asai et al. | 73/49.3 X |
| 5,345,814 | 9/1994 | Cur et al. | 73/49.3 |
| 5,499,529 | 3/1996 | Kronberg et al. | 73/40.7 |

FOREIGN PATENT DOCUMENTS 0445002  9/1991  European Pat. Off. .

OTHER PUBLICATIONS

Hanson, et al., "In Quest of Sterile Packaging: Part 1, Approaches to Package Testing", *Medical Device & Diagnostic Industry*, Aug. 1995, pp. 56–61.

Jones, et al., "In Quest of Sterile Packaging: Part 2, Physical Package Integrity Test Methods", *Medical Device & Diagnostic Industry*, Sep. 1995, pp. 81–85.

*Primary Examiner*—Daniel S. Larkin
*Attorney, Agent, or Firm*—Hamilton, Brook, Smith & Reynolds, P.C.

[57] ABSTRACT

A method and apparatus are directed to non-destructive testing for a leak in a sealed package having an interior chamber formed of a gas-permeable portion and a non-gas-permeable portion. A temporary barrier having an aperture is formed to the gas-permeable portion to temporarily seal the gas-permeable portion of the sealed package except at the aperture. A tracer gas is applied through the aperture at the gas-permeable portion, whereby the tracer gas enters into the interior chamber. The concentration of tracer gas is measured at the exterior of the sealed package, thereby testing for a leak in the sealed package.

33 Claims, 4 Drawing Sheets

METHOD AND APPARATUS FOR DETECTING LEAKS IN PACKAGING

RELATED APPLICATIONS

This present application claims priority to co-pending U.S. Provisional Patent Application No. 60/032,229, filed on Dec. 2, 1996; U.S. Provisional Patent Application No. 60/032,962, filed on Dec. 13, 1996; U.S. Provisional Patent Application No. 60/048,129, filed on May 30, 1997; and U.S. Provisional Patent Application No. 60/062,350, filed on Oct. 15, 1997. The entire teachings of each application are incorporated herein by reference.

BACKGROUND OF THE INVENTION

Gas sterilization is widely used for medical devices that must be sterile at time of use, but cannot be subjected to high temperature sterilization. Examples of such medical devices include cardiac pacemakers and catheter-based monitoring devices, such as blood pressure probes. Typically, the medical device is sealed within a package that is permeable to gases but impermeable to bacteria. The package is then placed within a gas sterilization chamber, and a sterilizing gas, such as ethylene oxide, is first introduced into the gas-permeable package to achieve sterilization, and is then removed from the gas-permeable package, leaving the interior of the package sterile but non-toxic.

In a typical design, the medical device is placed within a thermoformed rigid plastic tray equipped with a flat sealing flange. A sheet of gas-permeable membrane, such as du Pont TYVEK® 1073-B (medical grade) brand membrane, which is available from E.I. du Pont de Nemours & Co., is then sealed to the sealing flange, typically by using an adhesive. TYVEK membrane is a porous material fabricated as a mat of polyethylene fibers. It is permeable to gases, but its pores are tortuous paths that exclude bacteria.

The integrity of the seal is critically important to maintaining sterility. Leaks can result from incorrect setting of parameters in the automated sealing process, or from physical defects such as burrs on the face of the sealing equipment.

In current known practice, human inspectors perform one hundred percent visual inspection of the finished packages to look for defective seals, and statistical samples undergo destructive testing using microbial challenge techniques. Each of these techniques has important drawbacks. Visual inspection may not detect every type of leak, and human visual inspection is subject to potential lapses of attention by human inspectors. In microbial challenge methods, the package first is exposed to an aerosol of bacteria. The outside of the package is then cleaned, the package is opened, and interior samples are tested by microbial culturing. The microbial challenge methods are less sensitive than visual inspection, and are subject to false positives due to contamination from the exterior of the package. Recent articles in *Medical Device and Diagnostic Industry* have discussed the limitations of microbial challenge methods. (J. Spitz, "Relevance of Microbial Challenge Testing to Package Sterility," (January 1994, p.142); J. Spitzley, "How Effective is Microbial Challenge Testing for Intact Sterile Packaging?" (August 1993, p.44).

In other applications, leak detection is often done by placing a tracer gas during packaging inside a package to be tested, and detecting low levels of the tracer gas outside the package. Detection of low levels of gas leakage is difficult, in which the package is specifically designed to be highly permeable to gases. More specifically, one portion of the package, the TYVEK membrane sheeting, is designed to be gas-permeable in the direction perpendicular to the plane of the membrane. It is of interest to detect gas-permeable flaws or channels in the seal between the TYVEK membrane and the sealing flange of the rigid plastic tray, and it is of interest to detect gas-permeable flaws in the rigid plastic tray, such as a pin hole.

Therefore, a need exists for a method and apparatus for non-destructive testing for a leak in a sealed package having an interior chamber formed of a gas-permeable portion and a non-gas-permeable portion.

SUMMARY OF THE INVENTION

The present invention is directed to a method and apparatus for non-destructive testing for a leak in a sealed package having an interior chamber formed of a gas-permeable portion and a non-gas-permeable portion.

The method includes forming a temporary barrier having an aperture with the gas-permeable portion to temporarily seal the gas-permeable portion of the sealed package, except at the aperture. A tracer gas is applied through the aperture at the gas-permeable portion, whereby the tracer gas enters into the interior chamber. The concentration of tracer gas is measured at the exterior of the sealed package, thereby testing for a leak in the sealed package.

In another embodiment, a tracer gas is applied to a first section of the gas-permeable portion, whereby the tracer gas enters into the interior chamber of the sealed package. The concentration of the tracer gas is measured at a second section of the gas-permeable portion, thereby testing for a leak in the second section of the gas-permeable portion. The tracer gas is applied to the second section of the gas-permeable portion, whereby the tracer gas enters into the interior chamber. The concentration of the tracer gas is measured at the first section of the gas-permeable portion, thereby testing for a leak in the first section of the gas-permeable portion.

The apparatus includes a barrier layer for temporarily attaching to the gas-permeable portion of the sealed package and for forming a first region and a second region. An aperture is in the barrier layer through which a tracer gas can be moved from the first region to the second region. A tracer gas source is provided for supplying gas to the first region. A tracer gas analyzer for measuring the concentration of tracer gas is in the second region.

The present invention has many advantages including testing a sealed package for leaks without destroying it. Another advantage is that the sterility of the package contents can be maintained during testing.

DETAILED DESCRIPTION OF THE INVENTION

Figure 1:
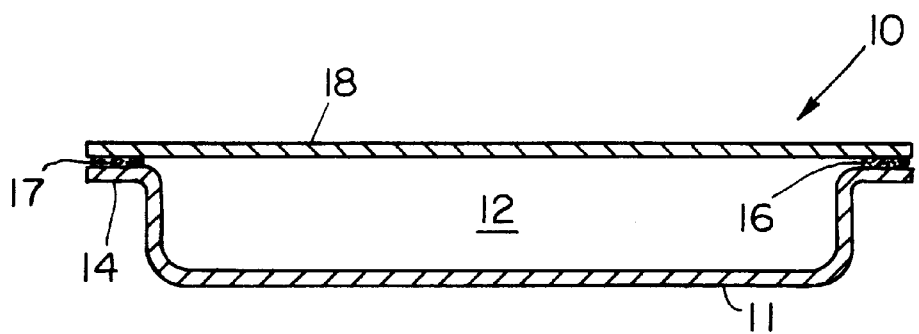
FIG. 1 is a cut-away side elevational view of a sealed package that can be tested with this invention.
Figure 2:
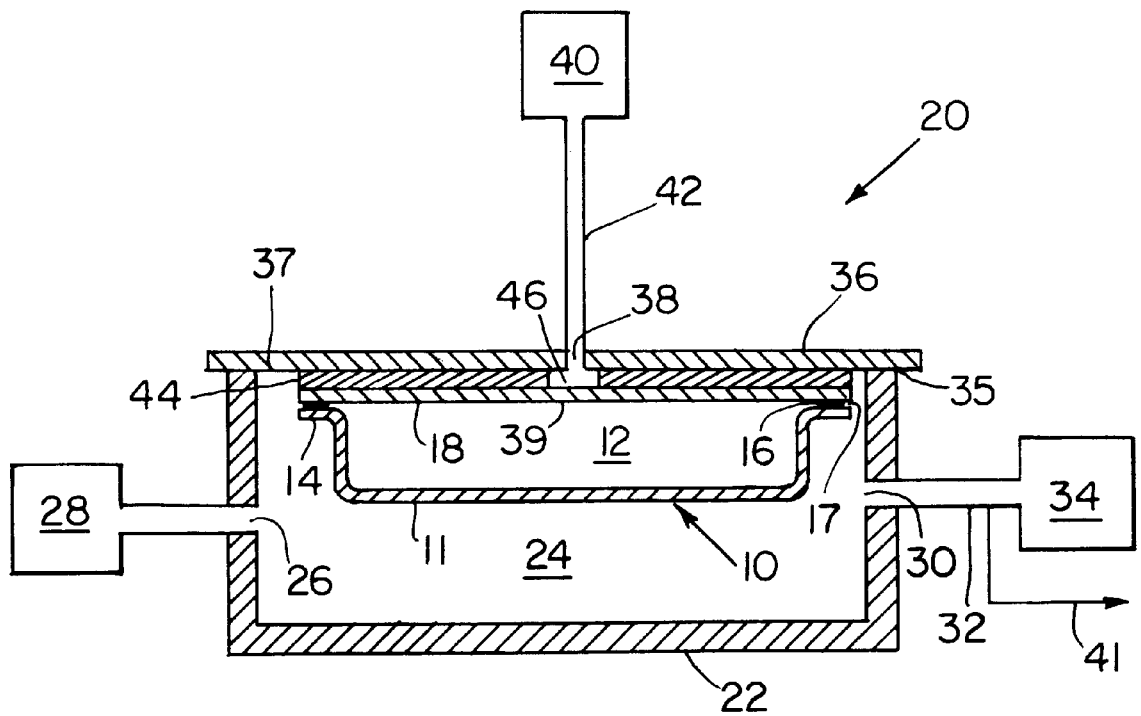
FIG. 2 is a cut-away side elevational view of a first embodiment of an apparatus for testing a sealed package for leaks.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention. All percentages and parts are by volume unless otherwise indicated.

The present invention relates to a method and apparatus for non-destructive testing of leaks in gas-permeable packaging, where such packaging includes a gas-permeable membrane, such as TYVEK membrane sheeting, sealed to a flange or other flat feature on a relatively gas-impermeable portion, such as a tray or relatively gas-impermeable flexible plastic film or other gas-impermeable portion of the packaging, such as a metal foil. Specifically, the invention relates to detection of leaks in the seal between the gas-permeable membrane and the tray or flexible plastic film, and leaks in the wall of the tray or flexible plastic film.

Many types of packages are suitable for use for testing with this invention. As shown in FIG. 1, sealed package 10 includes tray 11 which has chamber 12 suitably sized for holding a medical device or other item (not shown). Tray 11 is formed of a material that is non-permeable to gases under low pressure. Examples of materials include plastics, such as polyvinyl chloride, polyethylene, polypropylene, or polyethylene terepthalate (PET). Other types of materials include metal and metal foil linings. In another embodiment, tray 11 is formed of flexible non-permeable film. Tray 11 has sealing flange 14 for placement of adhesive sealant 16. Adhesive sealant 16 has exterior edge 17 or sealing bead. Tray 11 is sealed with a suitable adhesive, such as a heat seal polyolefin, to gas-permeable sheet 18. Gas-permeable sheet 18 is a porous membrane formed of a thermoplastic or paper that allows passage through the membrane of a gas but not larger particles, such as dust, bacteria, etc. In one embodiment, the preferred membrane is a mat of polyolefin fibers available from du Pont under the trademark TYVEK. Typically, gas-permeable sheet 18 has a thickness in the range of between about 0.127 and 0.254 millimeters (0.005 and 0.01 inches). Gas-permeable sheet 18 encloses package chamber 12.

Leak detection apparatus 20 which includes shell 22 has test chamber 24 which is sufficiently sized for holding sealed package 10. Shell 22 is made of a metal or other non-gas-permeable material. Shell 22 includes purge gas inlet 26 which is connected to purge gas source 28. Suitable purge gases include air, nitrogen, or other gases which can purge the tracer gas from test chamber 24. Shell 22 has gas outlet 30 for directing gas in test chamber 24 through outlet gas tube 32 to gas analyzer 34. Examples of a suitable gas analyzer includes a mass spectrometer. Outlet gas tube 32 has vent exit 41 for removing purge gas.

Platen 36, which is removable, covers shell 22 to provide seal 35 to enclose and to securely seal chamber 24 with sealed package 10 therewithin for testing. Tray 11 and exterior edge 17 of adhesive sealant 16 between sealing flange 14 and gas-permeable sheet 18 are exposed to the gas space within test chamber 24. Platen 36 includes platen aperture 38 which has an inlet for tracer gas. Platen aperture 38 is connected to tracer gas source 40 through tracer gas tube 42.

The tracer gas is chemically and biologically inert with no interreaction with the sealed package or its contents. Examples of suitable tracer gases include gases that can be detected in low concentrations by an instrument, such as a mass spectrometer or other analyzer. The tracer gas can include helium, neon, argon, krypton, xenon, or carbon dioxide, or freon-type fluorinated hydrocarbons. A preferred tracer gas has a concentration of less than one percent by volume in ambient air. A particularly preferred tracer gas has a concentration in ambient air of about 500 parts per million (ppm) or less by volume. For example, helium is typically present in air at a concentration of about five ppm by volume. In the present invention, the tracer gas is usually mixed with another gas, such as air, to form a tracer gas mixture that is relatively high in tracer gas concentration in comparison to the ambient air. In the tracer gas mixture, tracer gas typically has a concentration in the range of between 0.1 and 10 percent by volume. In one embodiment, the tracer gas is helium and is mixed with air. In a particularly preferred embodiment, the tracer gas mixture includes 2.5 percent by volume helium. Tracer gas source 40 can provide tracer gas at a total pressure of between about 12 and 1,000 millimeters (0.5 and forty inches) of water gauge to gas-permeable sheet 18. The flow of tracer gas mixture is controlled by suitable means known in the art.

Tracer gas analyzer 34 can be connected to a digital computer with a program that can receive the data from tracer gas analyzer 34 and compare it with previously measured data of tracer gas concentrations from sample sealed packages that are properly sealed.

Platen 36 has temporary barrier layer 44 that is applied to chamber side surface 37. Temporary barrier layer 44 is sized so that essentially all of gas-permeable sheet 18 is covered. Temporary barrier layer 44 has barrier layer aperture 46 that is aligned with platen aperture 38 for delivering tracer gas to the exposed portion 39 of gas-permeable sheet 18. Although sealed package 10 is shown attached under temporary barrier layer 44, the system can be inverted so that the sealed package 10 lies on temporary barrier layer 44. In one embodiment, barrier layer aperture 46 has a diameter in the range of between about 0.5 and 10 millimeters. A preferred diameter is about two millimeters. A preferred temporary barrier layer is a gas-impermeable tape with a thin coating of removable or repositionable adhesive that is commonly used in removable or repositionable labels, such as those supplied by Stickertape, 1430 Church St., Bohemia, N.Y. 11716-5000 or Scotch Brand No. 850 or No. 852 Polyester Tape, both supplied by Minnesota Mining and Manufacturing Industrial Tape and Specialties Division, 3M Center, Building 220-8E-04, St. Paul, Minn. 55144-1000. Preferably, the adhesive bonds to the gas-permeable sheet 18 to seal without voids or gaps in the region of the sealing bead of the sealed package. When the tape is removed after testing, the adhesive remains with the tape, while leaving little or no residue on the gas-permeable sheet 18.

Gas-permeable sheet 18 of sealed package 10 is positioned on temporary barrier layer 44 at barrier layer aperture 46. Sealed package 10 is placed inside test chamber 24 by platen 36 positioned against shell 22 of test chamber 24. Test chamber 24 is purged through vent exit 41 with a purge gas from purge gas source 28, such as nitrogen, that contains little or none of the tracer gas, until the atmosphere in test chamber 24 is essentially the purge gas only. The flow of purge gas is stopped by closing vent exit 41. Tracer gas mixture is directed from tracer gas source 40 through tracer gas tube 42 into package chamber 12 through exposed portion 39 of gas-permeable sheet 18. Tracer gas mixture is supplied to the exposed portion 39 at a pressure of between about 12 and 1,000 millimeters (0.5 and forty inches) of water gauge and the tracer gas flows into the sealed package until the pressure is equalized. Introduction of tracer gas can be accelerated by means of pressure or vacuum cycling as long as the pressure differentials are within the mechanical limits of the package. Sealed package 10 is allowed to remain inside chamber 24 for a predetermined length of time, typically between about one and one hundred seconds, to allow the concentration of tracer gas to build up inside the test chamber 24 if leaks are present at adhesive sealant 16 or in a pin hole or crack in tray 11.

The concentration of the tracer gas is measured by tracer gas analyzer using a mass spectrometer or other suitable instrument. In a preferred embodiment, the mass spectrometer is a quadrupole residual gas analyzer (rga) tuned for helium. A suitable device is available from Stanford Research Systems, Model No. RGA 100. The analyzer is usually serially data linked to a microcomputer for sending data. A microcomputer with a human interface, such as Windows, provides an environment for a display panel, data storage, and programs to compare test data with control samples. However, tracer gases other than helium can be used. For example, if carbon dioxide is used as a tracer gas, an infrared analyzer can be a suitable alternative to the mass spectrometer.

Gas transport is rapid across the plane of gas-permeable sheet 18. The rate of lateral transport of gases within the plane of gas-permeable sheet 18 is much lower, but still non-zero. When temporary barrier layer 44 is applied to the gas-permeable sheet 18, permeability across the plane of the gas-permeable sheet 18 is eliminated, but lateral permeability is not affected. Tray 11 can also have a slight permeability if formed of a plastic. For this reason, properly sealed packages can exhibit small but non-zero permeability, and defective packages exhibits much higher permeability. The concentration of tracer gas is compared with data for the concentration of prior tested sample packages that are properly sealed. Any statistically significant differences would indicate a leak.

Temporary barrier layer 44 is sealed in place against gas-permeable sheet 18 using a removable or repositionable adhesive rather than a compressed gasket. This is an important feature of the invention. It is important to isolate the flat portion of gas-permeable sheet 18 when performing leak testing on those portions of the package that must be inspected for gas-permeable flaws. However, if a compressed gasket were used, the compressive force might temporarily clamp the gas-permeable sheet 18 against the sealing flange on the plastic tray, thereby masking the presence of a leak.

Any tracer gas which leaks out through the sealing bead or through defects in the wall of the plastic tray is captured within the test chamber and detected by the measurement instrument. In the case of a massive leak, a massive concentration of tracer gas can be detected. Temporary barrier layer 44 should be discarded after each use, or after a limited number of uses, so that the adhesive coating remains clean and effective.

Figure 3:
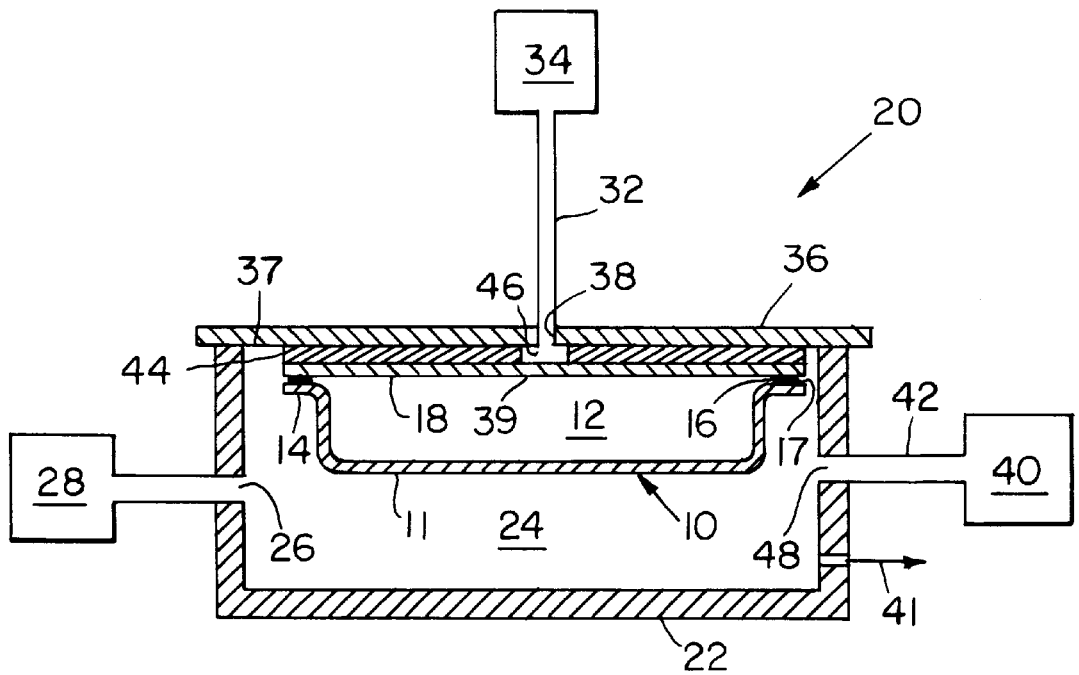
FIG. 3 is a cut-away side elevational view of a second embodiment of an apparatus for testing a sealed package for leaks.

As shown in FIG. 3, it is possible to reverse the placement of the tracer gas inlet and of the tracer gas analyzer. Vent exit 41 is in wall of shell 22 for venting the atmosphere in test chamber 24. In this embodiment, after purging, vent exit 41 is closed and tracer gas is directed first through tracer gas inlet 48 into test chamber 24 and then into sealed package 10, such as through a pin hole leak (not shown). Tracer gas that enters into sealed package 10 is directed through exposed portion 39 of gas-permeable sheet 18 at barrier layer aperture 46 to gas analyzer 34.

Figure 4:
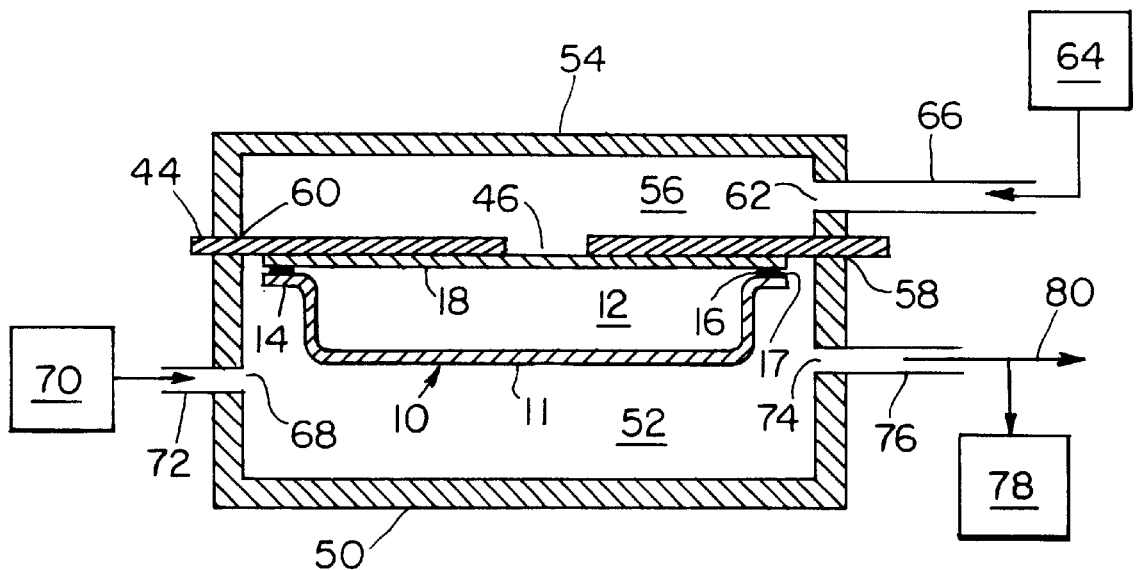
FIG. 4 is a cut-away side elevational view of a third embodiment of an apparatus for testing a sealed package for leaks.

In another embodiment, as shown in FIG. 4, temporary barrier layer 44 extends sufficiently beyond gas-permeable layer 18 to act as a barrier between lower shell 50 with lower chamber 52 and upper shell 54 with upper chamber 56. Temporary barrier layer 44 has barrier layer aperture 46 for allowing tracer gas to pass between package chamber 12 and upper chamber 56. Lower seal 58 is formed between lower shell 50 and temporary barrier layer 44. Upper seal 60 is formed between upper shell 54 and temporary barrier layer 44. Upper shell 54 has gas inlet 62 for directing a tracer gas mixture from tracer gas source 64 through tracer gas tube 66 into upper chamber 56. Lower shell 50 has purge gas inlet 68 for directing purge gas from purge gas source 70 through purge gas tube 72 into lower chamber 52. Lower shell 50 has gas outlet 74 for removal of gas from lower chamber 52. Outlet gas tube 76 is connected to gas analyzer 78 for directing gas to gas analyzer 78. Outlet gas tube 76 has vent exit 80 for removing purge gas.

Lower chamber 52 is purged with purge gas from purge gas source 70 through purge gas inlet 68 through gas outlet 74 to vent exit 80. Vent exit 80 is closed. Tracer gas mixture is directed from tracer gas source 64 to upper chamber 56 through tracer gas inlet 62 at a pressure greater than that in package chamber 12. Tracer gas mixture passes through package chamber 12 to lower chamber 52 by way of any channel leaks or holes in tray 11, if they exist, or by diffusion through the end edge of gas-permeable barrier 44. From lower chamber 52, gas is directed through gas outlet 74 to gas analyzer 78 for analysis of the gas for tracer gas to determine whether sufficient amount of tracer gas is present to indicate that a leak is present within sealed package 10.

Figure 5:
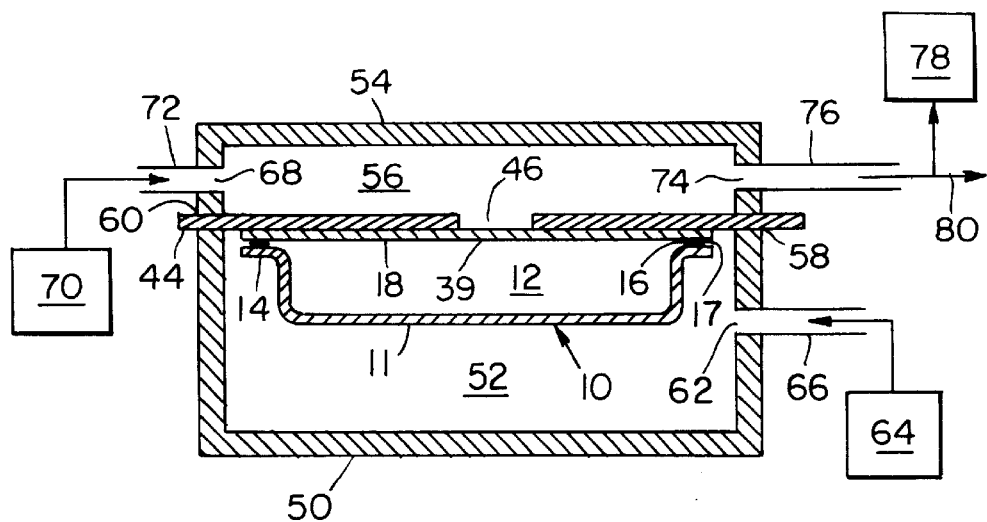
FIG. 5 is a cut-away side elevational view of a fourth embodiment of an apparatus for testing a sealed package for leaks.

As shown in FIG. 5, it is possible to reverse the placement of the tracer gas inlet and of the tracer gas analyzer. In this embodiment, tracer gas is directed into lower chamber 52 and into sealed package 10, such as through a pin hole leak (not shown). Tracer gas that enters into sealed package 10 is directed through exposed portion 39 of gas-permeable sheet 18 at barrier layer aperture 46.

The invention can be implemented for manual operation, partial automation or complete automation. The following is an embodiment for an automated scheme using a single test chamber: the sealed packages are delivered using a linear conveyor moving in the horizontal x-direction, with the gas-permeable sheet side up. The low-tack temporary barrier layer is delivered using a supply reel and a take-up reel, in the horizontal y-direction, positioned slightly above the displaced vertically above the packages to be tested. The conveyor and reel motions are stop/start rather than continuous, because a dwell in a fixed position is usually required at various points in the sequence. The temporary barrier layer is initially supplied as a continuous web. The temporary barrier layer transport passes a die-cut station to form a barrier layer aperture, prior to arrival over the package conveyor. The temporary barrier layer with an exposed adhesive is pressed against the gas-permeable sheet of the sealed package, and lifts it. The temporary barrier layer then carries the package in the y-direction to the test chamber, and the platen and test chamber are brought together on either side of the barrier layer web which holds the package. The measurement cycle is then carried out, including purging of the test chamber, introduction of tracer gas mixture, and measurement of tracer gas concentration within the test chamber. The test chamber and platen are then separated, and the barrier layer web resumes motion. Defective packages are stripped off the web at a first position, and acceptable packages are stripped off at a second position.

If greater throughput is needed, parallel processing using a linear or rectangular array of test chambers can be implemented using a similar scheme, except that the barrier layer web is wider, and a multiplicity of test packages are attached to the web in predefined locations, and then presented to a prepositioned array of test chambers and platens. Gas samples from each test chamber are sequentially indexed into the measuring instrument using a rotary sampling valve.

Often the size and number of the leaks to be detected are small and difficult to measure. Further, it is often desirable to determine the location of the leaks because they may be recurring in the same fixed locations places that can be corrected by a change in the sealing process or repair of a flow in the sealing apparatus. To accomplish this, a sampling probe can be employed to locally sample the tracer gas present about the sealed package. The sampling probe is deployed on a computer-controlled transport stage that allows the sampling probe to move. The sampling probe collects an air sample and transports the collected sample to a tracer gas detection instrument, such as a mass spectrometer helium leak detector.

Figure 6:
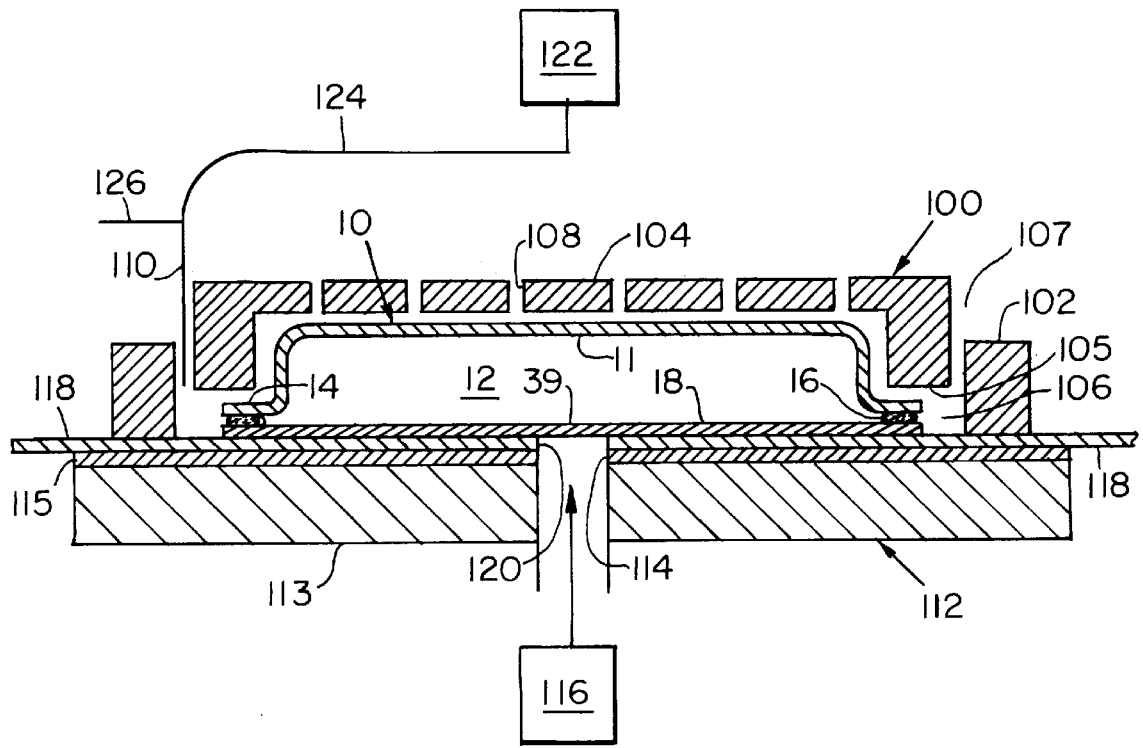
FIG. 6 is a cut-away side elevational view of a fifth embodiment of an apparatus for testing a sealed package for leaks.

Localized sampling within a test housing can be used to detect cracks in the tray. The test housing collects the tracer gas, thereby increasing the concentration of tracer gas available for measurement. Furthermore, if a test housing is not used, the gas plume can spew out in a localized direction that misses the programmed tracking of the sampling probe. As shown in FIG. 6, this can be done either by providing an array of access holes or access slits, or leaving the top of the test housing substantially open to permit free access by the sampling probe.

Sealed package 10 is placed in test housing 100. Test housing 100 includes housing perimeter barrier 102 and housing top barrier 104. Alternatively, test housing 100 can have only housing perimeter barrier 102. Housing perimeter barrier 102 has a height that is about the same as or greater than the thickness of sealed package 10. Lip 105 can apply a force to bond the test package 10 to the adhesive on temporary barrier layer 118 and to counteract any lift force that occurs when the interior of sealed package 10 is pressurized with tracer gas. Housing perimeter barrier 102 provides a barrier between proximal region 106 near sealed package 10 and the outside ambient atmosphere 107, which minimizes further dilution of tracer gas proximal to sealed package 10 during sampling and diffuses any directional gas plumes. Housing top barrier 104 covers sealed package 10. In one embodiment, the distance between housing top barrier 104 and sealed package 10 is in the range of between about two and ten millimeters. Housing top barrier 104 has access holes or access slits 108 that are sized for sampling probe 110 to enter slits 108 for local sampling for tracer gas from leaks in sealed package 10, particularly around sealing flange 14. In one embodiment, slits 108 have a width in the range of between about 0.076 and 0.152 millimeters (0.03 and 0.06 inches) and are spaced between about 6 and 25 millimeters (0.25 and one inches) apart. Slits 108 can run the length or width of test housing 100.

Base platen 112 has platen aperture 114 for directing tracer gas mixture from tracer gas source 116. Base platen 112 includes rigid plate 113 covered with elastomer layer 115, such as durometer 5 rubber, typically two to twenty millimeters thick. Elastomer layer 115 provides a compliant base for temporary barrier layer 118. Temporary barrier layer 118 is positioned between gas-permeable sheet 18 and base platen 112. Temporary barrier layer 118 has barrier layer aperture 120 that is positioned at platen aperture 114.

Sampling probe 110 is formed of a metal capillary, such as a stainless steel hypodermic needle gauge tubing. Probe tube 124 is a strong, flexible capillary tube, such as polyimide-coated fused silica tubing commonly used in capillary gas chromatography. Probe tube 124 is coaxially inside sampling probe 110, and extends a distance of between about one to ten millimeters beyond the tip of the sampling probe.

Sampling probe 110 is connected to tracer gas analyzer 122 by probe tube 124. Probe tube 124 is formed of a sufficiently flexible material to allow sampling probe 110 to move about test housing 100. Further, probe tube 124 is sufficiently short to minimize transport time without loss of sample integrity. Tracer gas analyzer 124 should have a fast transport time and be quick flushing for rapid sampling and analysis. Example of a suitable analyzer is a mass spectrometer from Stanford Research Systems, Model No. RGA 100.

Sampling probe 110 is mounted on transport stage 126 10 that is computer controlled. Transport stage 126 can move sampling probe 110 in an x,y,z direction for sampling regions proximal to sealed package 10. An example of a suitable transport stage is available from IAI America.

Sealed package 10 is placed in the test housing 100 and the gas-permeable layer 18 is temporarily bonded to the temporary barrier layer 118, as described above.

Tracer gas mixture is introduced into sealed package 10 via exposed portion 39 of gas-permeable sheet 118 to achieve a predetermined pressure within the package. Preferably, the tracer gas is helium, and the predetermined pressure is in the range of about 2.5 and 1,000 millimeters (0.1 to 40 inches) of water greater than ambient pressure. In a particularly preferred embodiment, the helium gas is 2.5%, by volume, and has a total pressure of about 254 millimeters (ten inches) of water gauge.

Figure 7:
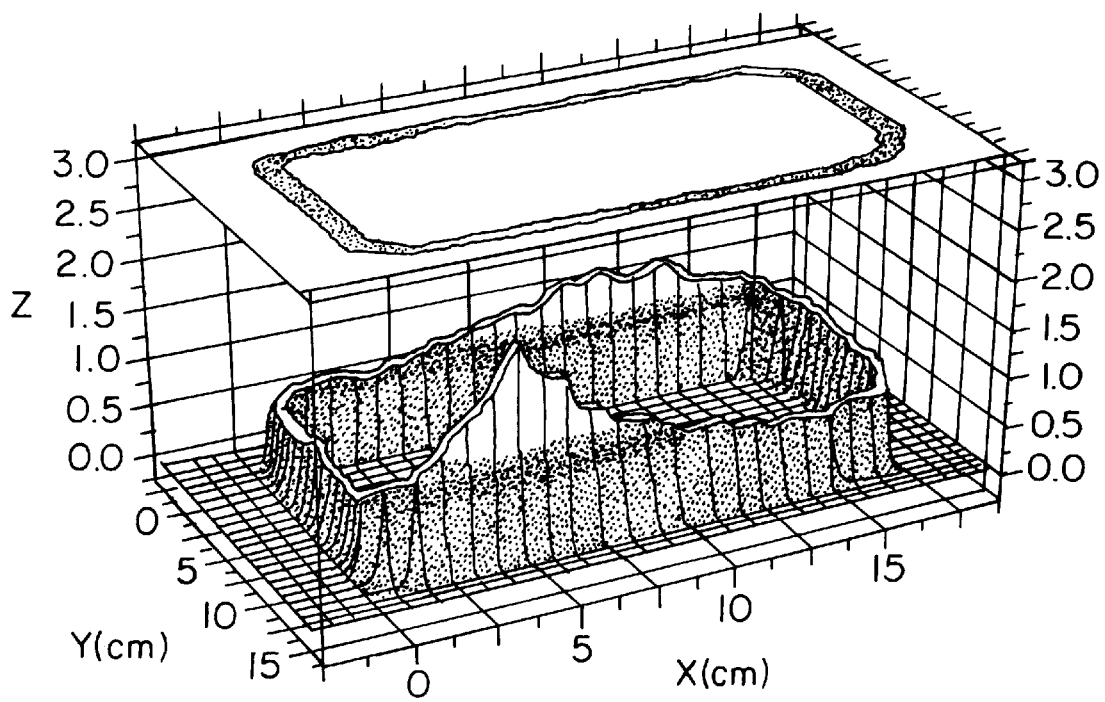
FIG. 7 is a perspective plot of helium concentration along the perimeter of the sealing bead of a tested sealed package.

After a waiting period in the range of between about one and 100 seconds, and preferably 10 seconds, sampling probe 110 is moved along the periphery of the adhesive sealant by means of computer-controlled transport stage 126. In one embodiment, transport stage 126 moves sampling probe 110 at a rate in the range of between about 25.4 and 254 millimeters (one and ten inches) per second. As sampling probe 110 is moved, the tracer gas analyzer 122 monitors the concentration of tracer gas as a function of position along the periphery of adhesive sealant 16. Localized defects in the seal, such as channels, are detected as localized peaks in the tracer gas concentration as a function of position. FIG. 7 shows a plot of relative helium concentration stated in dimensionless values (z) along the perimeter (x,y) of the sealing bead of the sealed package in centimeters. Non-localized defects, such as a heat seal that has not been heated sufficiently, are detected as a higher than normal tracer gas concentration all along the seal.

Figure 8:
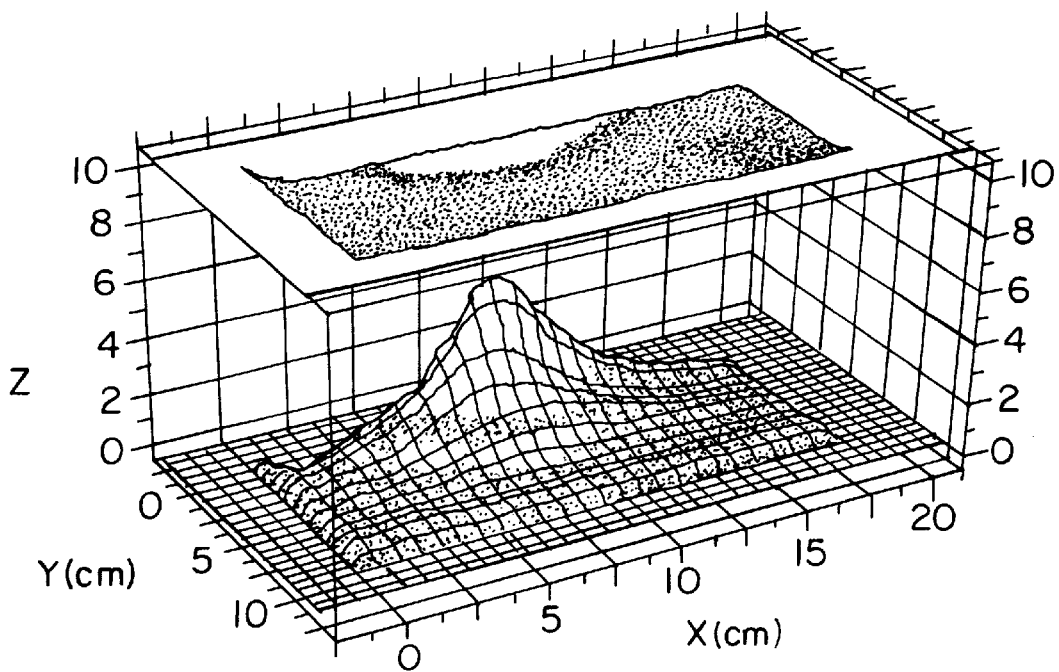
FIG. 8 is a perspective plot of helium concentration across the top of the tray of the tested sealed package.

After inspecting the periphery of adhesive sealant 16, sampling probe 110 is deployed to detect cracks or other leaks in tray 11 of sealed package 10. There are several alternative ways to sample for cracks: (a) bulk detection within the concave test housing 100, (b) localized sampling through an array of holes or slits provided in housing top barrier 104 of test housing 100, and (c) localized sampling by moving sampling probe 110 along the top of the tray using free access provided by the substantially open test housing 100. FIG. 8 shows a plot of helium concentration (z) across the top of the tray of the sealed package as a function of position (x,y) in centimeters.

Within the sterile packaging industry, defect detection methods are validated by using test samples with intentional channels running across the sealing beads, such as channels formed by 0.127 and 0.076 millimeter (5-mil and 3-mil) diameter wire, and by human hair having an approximate diameter of two mils. The channel defect is prepared by heat sealing the wire or hair into the sealing bead, and then pulling out the wire or hair to leave a channel of defined diameter.

Bulk detection methods using configurations as disclosed in FIGS. 2–5 were unable to detect 0.127 millimeter (5-mil) channel defects, because the bulk measurement is dominated by the basal leak rate of gas-permeable sheet 18 about its edges. When localized scanning is used, detection of 0.127 millimeter (5-mil) defects was reliable. However, detection of 0.076 millimeter (3-mil) defects was marginal, and human-hair sized defects could not be detected at all. These tests were performed with the package pressure set to 25.4 millimeters (one inch) of water above ambient pressure.

The effect of package pressure was then studied experimentally. In the pressure range of between about zero and 254 millimeters (zero to ten inches) of water gauge, the basal leak rate changes only slightly, but the leak rate from channel defects increases strongly with increasing pressure.

The automated test procedure is modified to take advantage of these observations. Scans of helium concentration as a function of position are recorded under two conditions of pressurization: 254 millimeters (ten inches) of water gauge and zero millimeters (zero inches) of water gauge. Channel defects are readily detected by comparing the two traces. The defects appear as peaks in ratio or difference plots.

This approach was successful for reliable detection of the channel defects tested, including 0.076 millimeter (3-mil) and human hair diameters. The use of two scans at different pressures cancels out the effect of systematic variations in the basal leak rate, and improves the detection limit. However, for many purposes, it is sufficient to use only the scan at higher pressure, and detect leaks using signal processing techniques to recognize peaks. This results in a shorter overall measurement time.

As discussed above, cracks in the pressure-formed tray are detected by measuring the tracer gas concentration in a pooled air volume inside test housing that surrounds the outside of the tray. This is effective for many of the cracks. However, the pooled air volume develops a slight basal concentration of helium, even in the absence of cracks, apparently due to slight permeability of the intact tray. Because of this, localized sampling is needed to detect the smallest cracks of interest.

For localized sampling, an array of access holes or slots are provided in the test housing, and the sampling probe is deployed to sample either a multiplicity of holes or a continuous path along the slots. In this arrangement, the test housing is used to collect and store the sample. Alternatively, the test housing can be substantially open on top, so that the tray surface can be sampled freely by moving the sampling probe under computer control.

Either approach is effective for detection of cracks in tray 11. If test housing 100 is substantially open, the test package should be actively pressurized while sampling probe 110 is deployed in a sampling pattern. If test package 10 is substantially closed, sampling can also be carried out after the pressure in the test package has been vented. Thus, if two successive scans, one at high pressure and one at low pressure, are used to detect channel defects in the sealing bead of sealing adhesive 16, tray 11 can be scanned during the time interval required for venting of the test package after the high pressure scan, thus reducing the time required for testing.

In an automated embodiment, temporary barrier tape 118 is moved across the platen 112 by means of a bi-directional reel-to-reel drive. During the test cycle, barrier layer aperture 120 is formed in the center of temporary barrier layer 118, and the sealed package 10 is secured on temporary barrier layer 118. After sealed package 10 is tested, temporary barrier layer 118 is advanced, and sealed package 10 is released as temporary barrier layer 118 passes around a roller. Barrier layer 118 is then moved back across platen 112 so that the same portion of barrier layer 118 can be reused to test the next sealed package. After a predetermined number of uses, the tape drive is advanced to expose a fresh section of barrier layer. When a fresh section of tape is used for the first time, a hole is punctured in the central portion of the tape.

There are two alternative designs for the top of the test housing, substantially open, and substantially closed. A yoke structure supports the test housing. The yoke structure is provided with means to rotate on its horizontal axis and means to translate up and down. Means are provided to apply two different levels of downward force to housing top barrier 104 of test housing 100, for example, by varying the air supply pressure to a pneumatic actuator. A greater force applied by lip 105 is used to bond the test package to the adhesive on the temporary barrier layer. A lesser force applied by lip 105 is used to counteract the lifting force that occurs when the interior of sealed package 10 is pressurized with tracer gas while not excessively compressing the seal.

An operating cycle for testing a package can include a human operator (or optionally a robotic mechanism such as a pick-and-place mechanism) placing a test package into the test housing with the tray face down and gas-permeable sheet face up. A suction cup pulls the test package into the test housing, thereby positioning and securing the test package within the test housing. The yoke structure rotates, so that the test package is now positioned close to the platen, with gas-permeable sheet face down. The yoke structure is translated downward, and the greater force level is applied to the test housing, thus pressing the sealing flange region of the gas-permeable sheet against a temporary barrier layer the adhesive layer on the barrier tape. The greater force level is released, and the lesser force is applied to the test housing, to counteract lifting forces that occur when the sealed package is pressurized with tracer gas. The sampling probe is deployed to measure tracer gas concentrations as a function of position along the periphery of the sealing bead to detect seal defects and along the exterior of the tray to detect tray cracks. When the measurement is finished, the yoke assembly is translated up to lift the test housing off the test package on the tape. The test housing, now empty, is rotated up, and is now ready to receive the next test package. The tape now advances to release the test package from the tape, and then rewinds to be reused for the next test package.

The gas-permeable sheet can also be tested for pinhole leaks or other breaks. The gas-permeable sheet is tested by applying a tracer gas mixture to a portion of the gas-permeable sheet and scanning the remainder of the gas-permeable sheet with a sampling probe and the gas is analyzed. Then the tracer gas mixture is applied to a second portion of the gas-permeable sheet and the portion where the tracer gas mixture was previously applied is now scanned by the sampling probe and the gas is analyzed.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

We claim:

1. A method for non-destructive testing for a leak in a sealed package having an interior chamber formed of a gas-permeable portion and a non-gas-permeable portion, comprising the steps of:
   a) forming a temporary barrier having an aperture to the gas-permeable portion to temporarily seal the gas-permeable portion of said package except at said aperture;
   b) applying a tracer gas through said aperture at said gas-permeable portion, whereby said tracer gas enters into said interior chamber; and
   c) measuring the concentration of tracer gas at the exterior of the sealed package, thereby testing for a leak in the sealed package.

2. The method of claim 1 wherein the tracer gas is selected from a group consisting of gases having a concentration of less than about one part per thousand by volume in an ambient atmosphere and is chemically inert with the sealed package.

3. The method of claim 1 wherein the tracer gas is selected from a group consisting of helium, neon, argon, krypton, xenon, and carbon dioxide.

4. The method of claim 1 wherein the tracer gas includes a fluorinated hydrocarbon.

5. The method of claim 1 wherein the temporary barrier includes a sheet having a removable adhesive on at least one side.

6. The method of claim 1 wherein the concentration of the tracer gas is measured by a mass spectrometer.

7. The method of claim 1 wherein the concentration of the tracer gas is measured by an infrared light analyzer.

8. The method of claim 1 wherein the gas-permeable portion of said sealed package is formed with a material selected from the group consisting of paper and a polyolefin mat.

9. The method of claim 1 wherein the non-gas-permeable portion of said sealed package is formed from a polymer selected from the group of polyethylene, polypropylene, polyvinyl chloride, and polyethylene terepthalate.

10. The method of claim 1 wherein said tracer gas is applied in a gas mixture at a pressure in the range of between about 12 and 1,000 millimeters (0.5 and 40 inches) of water gauge.

11. The method of claim 1 wherein the concentration of the tracer gas is measured with a sampling probe proximal to the exterior of the sealed package.

12. The method of claim 11 wherein the sampling probe is moved by a transport stage about the periphery of the sealed package while measuring the tracer gas.

13. The method of claim 12 wherein the sealed package is placed in a housing while measuring the tracer gas.

14. The method of claim 13 wherein the tracer gas is measured in the housing through a plurality of ports by the sampling probe.

15. The method of claim 14 wherein said ports are selected from a group consisting of slits and holes.

16. The method of claim 1 wherein the atmosphere proximal to said sealed package is purged with a purge gas prior to applying the tracer gas.

17. The method of claim 16 wherein the purge gas is selected from the group consisting of air and nitrogen.

18. A method for non-destructive testing for a leak in a sealed package having an interior chamber formed of a gas-permeable portion and a non-gas-permeable portion, comprising the steps of:
   a) applying a temporary barrier having an aperture to the gas-permeable portion to temporarily seal the gas-permeable portion of said package;
   b) applying a tracer gas under pressure through said aperture to said gas-permeable portion whereby said tracer gas enters into said interior chamber;
   c) purging the atmosphere adjacent to said sealed package of the tracer gas; and
   d) measuring the concentration of the tracer gas proximal to the exterior of the sealed package, thereby testing for a leak in the sealed package.

19. A method for non-destructive testing for a leak in a sealed package having an interior chamber formed of a gas-permeable portion and a non-gas-permeable portion, comprising the steps of:
   a) applying a tracer gas to a first section of the gas-permeable portion, whereby said tracer gas enters into said interior chamber; and
   b) measuring the concentration of the tracer gas at a second section of the gas-permeable portion, thereby testing for a leak in the second section of the gas-permeable portion.

20. The method of claim 19 wherein the method further comprises the steps of:
   c) applying a tracer gas to the second section of the gas-permeable portion, whereby said tracer gas enters into said interior chamber; and
   d) measuring the concentration of the tracer gas at the first section of the gas-permeable portion, thereby testing for a leak in the first section of the gas-permeable portion.

21. An apparatus for non-destructive testing for a leak in a sealed package having a gas-permeable portion and a non-gas-permeable portion, comprising:
   a) a barrier layer for temporarily attaching to the gas-permeable portion of said sealed package;
   b) an aperture in said barrier layer through which a tracer gas can be directed into said sealed package;
   c) a tracer gas source for supplying a tracer gas to within said sealed package; and
   d) a tracer gas analyzer for measuring the concentration of tracer gas outside said sealed package.

22. The apparatus of claim 21 wherein the tracer gas is selected from a group consisting of gases having concentrations of less than about one part per thousand by volume in ambient air and is chemically inert with the sealed package.

23. The apparatus of claim 22 wherein the tracer gas is selected from a group consisting of helium, neon, argon, krypton, xenon, and carbon dioxide.

24. The apparatus of claim 21 wherein the temporary barrier includes a sheet having an adhesive on at least one side that allows the temporary barrier to bond and then be removable from the gas-permeable barrier.

25. The apparatus of claim 21 wherein the tracer gas analyzer is selected from a group consisting of a mass spectrometer and infrared light analyzer.

26. The apparatus of claim 21 wherein the gas-permeable portion of said sealed package is formed with a material selected from the group consisting of paper and a polyolefin mat.

27. The apparatus of claim 21 wherein the non-gas-permeable portion of said sealed package is formed from a polymer selected from the group of polyethylene, polypropylene, polyvinyl chloride, and polyethylene terepthalate.

28. The apparatus of claim 21 wherein the tracer gas analyzer includes a sampling probe for measuring the concentration of the tracer gas proximal to the exterior of the sealed package.

29. The apparatus of claim 28 wherein the sampling probe is mounted on a transport stage for moving the sampling probe about the periphery of the sealed package while measuring the tracer gas.

30. The apparatus of claim 21 wherein the apparatus further includes a housing for enclosing the sealed package while measuring the tracer gas.

31. The apparatus of claim 30 wherein the housing includes a plurality of ports for inserting a sampling probe to measure the tracer gas proximal to the sealed package.

32. The apparatus of claim 31 wherein said ports are selected from a group consisting of slits and holes.

33. An apparatus for non-destructive testing for a leak in a sealed package having a gas-permeable portion and a non-gas-permeable portion, comprising:

a) a shell sized for holding said sealed package therein;

b) a platen for sealing said shell;

c) a platen aperture through said platen;

d) a barrier layer having a first barrier side for attaching to said platen and a second barrier side for temporarily attaching to said gas-permeable portion of said sealed package, wherein said barrier layer has an aperture aligned with said platen aperture;

e) a tracer gas source for delivering a tracer gas to the first side of said aperture; and f) a tracer gas analyzer for measuring the concentration of tracer gas on the second side of barrier layer.

* * * * *